United States Patent [19]
Abert et al.

[11] Patent Number: 4,789,649
[45] Date of Patent: Dec. 6, 1988

[54] MICACEOUS-CORDIERITE-GLASS CERAMIC

[75] Inventors: Christine Abert, Berlin; Eggert Beleites, Maua; Gunter Carl, Jena-Lobeda; Steffen Grosse, Berlin; Hilmar Gudziol, Jena; Wolfram Hoeland, Jena-Lobeda; Michael Hopp, Binz; Ralf Jacobi, Goerlitz; Harry Jungto, Jena; Guenther Knak, Berlin; Lutz Kreisel, Jena; Rudolf Musil, Jena; Karin Naumann, Jena; Frank Vogel, Brandenburg; Werner Vogel, Jena, all of German Democratic Rep.

[73] Assignee: Veb Jenaer Glaswerk, Jena, German Democratic Rep.

[21] Appl. No.: 894,976

[22] Filed: Aug. 8, 1986

[30] Foreign Application Priority Data

| Nov. 4, 1985 [DD] | German Democratic Rep. | 2824047 |
| Nov. 4, 1985 [DD] | German Democratic Rep. | 2824006 |
| Nov. 4, 1985 [DD] | German Democratic Rep. | 2824014 |
| Nov. 4, 1985 [DD] | German Democratic Rep. | 2824022 |
| Nov. 4, 1985 [DD] | German Democratic Rep. | 2824030 |

[51] Int. Cl.$^4$ ............... C03C 10/16; C03C 13/08; C09K 3/00
[52] U.S. Cl. ................................ 501/3; 501/4; 501/9; 106/35; 433/201.1; 433/202.1; 433/212.1; 433/218; 433/222.1
[58] Field of Search ............ 501/3, 4, 9; 106/35; 433/201.1, 202.1, 212.1, 218, 222.1; 428/432

[56] References Cited

U.S. PATENT DOCUMENTS 4,120,730 10/1978 Trojer et al. ................ 501/3
4,431,420 2/1984 Adair ......................... 501/3

Primary Examiner—Ferris H. Lander
Attorney, Agent, or Firm—Jordan and Hamburg

[57] ABSTRACT

Micaceous-cordierite-glass ceramic particularly suitable for stomatological, head surgery and neck surgery applicatiosn has a fracture toughness $K_{IC}$ of up to 2.0 MPa m$^{\frac{1}{2}}$, a hardness $HV_{0.07}$ of 300–1000, a compressive strength of up to 450 N/mm$^2$, a linear thermal expansion coefficient of 75–125×10$^{-7}$ K$^{-1}$, good chemical stability and excellent machinability as well as a high resistance to wear and comprises a composition in weight percentages of

| | |
|---|---|
| SiO$_2$ | 43–50 |
| Al$_2$O$_3$ | 26–30 |
| MgO | 11–15 |
| R$_2$O | 7–10.5 |
| F$^-$ | 3.3–4.8 |
| Cl$^-$ | 0.01–0.6 |
| CaO | 0.1–3 |
| P$_2$O$_5$ | 0.1–5 | wherein R$_2$O is the sum of 3 to 5.5 wt. % Na$_2$O and 4 to 6 wt. % K$_2$O, a first crystal phase of mica, and a second crystal phase of 5 to 30 volume % cordierite, wherein relatively large mica crystals of 10 to 200 μm are embedded in the glass and cordierite crystals of 0.5 to 5 μm are arranged in the glass.

48 Claims, 5 Drawing Sheets

MICACEOUS-CORDIERITE-GLASS CERAMIC

The invention relates to a micaceous-cordierite-glass ceramic which, because of its properties, is most extensively used in the machine construction and apparatus construction industries, but also as biocompatible material for medical purposes. It is preferably used for stomatological purposes, such as, for example, for tooth restorations, in particular, for inlays, crowns, tooth constructions, bridges and as veneer laminates for the tooth-colored veneering of artificial teeth, metal frameworks or natural teeth, furthermore, in dental orthopedics/orthodontics, preferably for adhesive brackets and small adhesive buttons, as fixation points at the tooth enamel for therapy with apparatus which is to be firmly attached and as implant material for head surgery and neck surgery as permanent hard tissue replacement for ear surgery, nose surgery, surgery of the paranasal sinuses, surgery of the base of the skull, and tracheal surgery.

BACKGROUND OF THE INVENTION AND RELATED ART

Glass ceramics containing mica or glass ceramics containing cordierite as the main crystal phase are known. For example, according to DE-OS No. 2,915,570, because of the low linear thermal expansion coefficient of the cordierite crystals, cordierite-glass ceramics have very good thermal properties, such as, for example, a linear thermal expansion coefficient of $12 \times 10^{-7} K^{-1}$.

At the same time, in cordierite-glass ceramics, such as, for example, according to U.S. Pat. No. 4,304,603 and DE-PS No. 3,130,977, such advantageous stress ranges can be produced in glass ceramic material that it is possible to produce a material of considerable strengths of 250-300 MPa, whereby tensile strengths, i.e. $K_{IC}$ values of up to 2.5 MPa m$^{\frac{1}{2}}$ are attained. These glass ceramics containing cordierite as the main crystal phase, however, are not workable by machines, i.e., they cannot be shaped by conventional hard metal tools.

As glass ceramic materials with advantageous machineability properties are known micaceous-glass ceramics, for example, according to DE-AS No. 2,133,652, DE-OS No. 2,224,990 and DD-WP No. 113,885.

Because of the easy cleavability of the flat mica sheets and the "card-house arrangement" of the mica crystals in the glass ceramic, good machineability of the materials is possible with hard metal tools. A considerable improvement of the machineability as compared to the glass ceramics with flat mica sheets, such as, for example, DE-AS No. 2,133,652, DE-OS No. 2,224,990, DD-WP No. 113,885, and such glass ceramics which have almost isolated spherical accumulations of fluorophlogopite crystals (such as shown in U.S. Pat. No. 3,325,265) have been attained by the development of a glass ceramic which has a new type of bent fluorophlogopite crystals. Such glass ceramics, as shown in the Patentschrift DD-WP No. 153,108 and subsequent publications, such as Glass Technology 24 (1983) 318, have a structure in which the bent fluorophlogopite crystals measuring 25-100 μm are embedded in optimum concentration in the residual glass matrix and the crystals are touching, so that the best conditions for an optimum machineability are created.

Although DD-WP No. 153,108, has attained an optimum for micaceous-glass ceramics with respect to machineability properties, for a broad range of applications, in particular also for medical uses, of glass ceramics as construction material which can be machined, especially the fracture bending, the hardness, the compressive strength, the wear properties and the linear thermal expansion coefficient of the materials are still insufficient.

In stomatology, as materials for inlays, crowns, tooth constructions and bridges are used preferably precious metals and alloys thereof, vitrified ceramics and organic polymers. However, these materials have considerable shortcomings. Precious metals are expensive, have a high thermal conductivity and their color is not always aesthetically satisfactory. The vitrified ceramics are not machineable with conventional hard metal tools and have disadvantages in the processing due to the occurring shrinkage process. Above all, the organic polymers have an insufficient mechanical strength.

Also the glass ceramics described in the U.S. Pat. No. 4,431,420 and in EP-PS No. 22.655, as well as in U.S. Pat. No. 4,515,634 and DE-OS No. 3,435,348 have considerable disadvantages with respect to the application in stomatology, because their properties are not adapted at an optimum to those of tooth enamel. This is the case, for example, with the tetrasilicic-acid-mica-glass ceramic described in U.S. Pat. No. 4,431,420 and EP-PS No. 22,655, for the linear thermal expansion coefficient of which, (according to "The Intern. J. of Periodontics and Restorat. Dent. 2(84) 36") is $72 \times 10^{-7} K^{-1}$ and which, therefore, is considerably below the value of tooth enamel of $114 \times 10^{-7} K^{-1}$. Such big differences are the cause of uncontrolled stresses between the tooth and the glass ceramic which, already at the slightest temperature differences, can cause the material to break and can induce the formation of peripheral cracks. Furthermore, the bending strength of this glass ceramic of 50-55 MPa is insufficient for a broad extensive application in stomatology, especially for thin-walled shaped bodies. Another disdavantage of the tetrasilicic-acid-mica-glass ceramic is that, obviously due to the problematic nature of expansion, there cannot be produced any compound material with high-strength parent substances, such as, for instance, corundum or metals.

It is known of glass ceramics containing fluorophlogopite, such as described, for example, in DD-WP No. 113,885 and DD-WP No. 153,108, that they have very good workability properties and parameters such that they are used, for instance, in apparatus construction and machine construction. An application of these materials for stomatologic purposes, however, would lead to considerable disadvantages due to properties which are not optimally adjusted to tooth enamel, for example, thermal properties and hardness.

Besides synthetic resins, there are used predominantly vitrified ceramics as materials for veneer laminates.

Veneer laminates made of vitrified ceramics have been industrially manufactured for the first time after the synthetic resins Hekodent (1935), Paladon (1937/38) and Palapont (1940) were introduced into dentistry as so-called Schroeder's hollow teeth (Cavidens). They serve as outer veneer laminates for artificial teeth made of the above-mentioned synthetic materials in order to compensate for the still insufficient abrasion strength.

Individually produced veneer crowns made of vitrified ceramic were also verifiable at that time, whereby the introduction of the so-called veneer ceramic by Schroeder in 1932 has furthered this veneering technology. As a reaction to the unsatisfactory long-term results of synthetic veneering, during the time period from 1952 to 1969, there was noticeable a preference for veneer laminates made of vitrified ceramic for veneer crowns, whereby there mainly occurred a reversal to finished products made of vitrified ceramic, such as gold-button teeth and platinum long-pin teeth. The system of mineral-faced crowns, which was introduced then, was based on definite end-shapes of veneer bodies which were obtained by grinding out the inside of the above-mentioned full-bodied teeth (Reumuth, E. and E. Arnold: Die Rostocker Facettenkrone. Dtsch. Stomat. 13 (1963) 391-398/Armbrecht, E. and A. Gerber: Die Schweriner Facettenkrone. Zahntechnik (Berlin) 5 (1964) 93-103). With the development and introduction to the market of the so-called metal ceramic, there was established a reduction in veneer technology in the countries with sufficient availability of the metal ceramic, whereas in countries where it was not available, it induced an industrial production of facing veneers made of vitrified ceramic in order to facilitate the work of the dental technician (Richter, H.: die Keracette, eine keramische Zahnschale. Zahntechnik (Berlin) 17 (1976) 313-316). The availability of composite synthetic materials, together with the introduction of adhesive techniques to clinical practice and dentistry led to the introduction to the market of laminates made of vitrified ceramic of a new type which were usually used for "front-side restorations", generally for front teeth, by the dentist himself (Calamia. J. R.: Etched porcelain veneers: The current state of art. Quint. Int. 16 (1985) 5-12).

Vitrified ceramic facing veneers cannot be produced industrially below a minimum thickness of 1.5 to 2 mm. Therefore, they are unsuitable for an outer layer made of ceramic of a compound shell.

S. Hobo, and T. Iwata described a hydroxyl-apatite-glass ceramic which, by means of casting technology can be shaped into veneer laminates for facing visible tooth surfaces (S. Hobo, and T. Iwata, Castable Apatite Ceramics As A New Biocompatible Restorative Material, I. Theoretical Considerations, in Quit.

Int. 16 (1985) 135-141). This glass ceramic is especially explained for an individual production technology and permits only the production of veneer laminates of greater wall strengths, similar to those made of vitrified ceramics, and is not suitable for industrial production technologies and backing it with layers of synthetic resin of compound materials, for instance, in order to improve the state of the color. A utilization of the already mentioned glass ceramics (U.S. Pat. No. 4,431,420, EP No. 22,655, U.S. Pat. No. 4,515,634, DE-OS No. 3,435,348, DD-WP No. 113,885 and DD-WP No. 153,108) is not known for facing shells and the above-mentioned deficiencies would also have a negative effect in case of such use.

As materials for adhesive brackets have been described up to now metal, synthetic resin and vitrified ceramic. At the present, there are used mainly tooth adjustment elements made of metal because they have good mechanical stability and a low friction of the adjustment arch in the slit. In order to attain sufficient bonding strengths for orthodontal adhesives, the preparation of the base surfaces of the tooth adjustment elements made of metal requires expensive and complicated technological methods, such as, for example, according to DE-OS No. 2,618,952, the production of peripheral perforated bases or the creation of retentive network bases, photo-etched spherical indentations, for instance, according to DE-OS No. 2,910,070, or wedge-shaped thread grooves. Because of the utilization of these expensive technologies there can be attained bonding strengths of up to a maximum of 12.3 MPa in adhesive metal brackets (Diedrich, P. and Dickmeiss, B. in Fortschr. Kieferorthop. 44 (1983), 298-310). One of the problems in the utilization of adhesive metal brackets has proven to be that various corrosion phenomena occurred on the brackets and caused permanent discoloration of the tooth enamel which, according to Kappert et al. (Fortschr. Kieferorthop. 45 (1984), 271-283) can be attributed to traces of Cr and Fe. The aesthetically unfavorable effect of metal tooth adjustment elements can be improved according to U.S. Pat. No. 4,527,975 by means of a facing made of tooth-colored synthetic resin which, however, in addition to the considerably greater material and time expenditures for the production and incorporation of this facing also considerably increases the risk of dental caries for the patient. In comparison to metal brackets, synthetic brackets, for example, according to GB-Patent No. 1,506,772, have a much more favorable aesthetic effect which, however, can be strongly reduced because of a discoloration of the synthetic resin due to foodstuff and coffee, tea, cigarettes, etc. Another disadvantage of synthetic brackets, furthermore, is their low mechanical strength which, according to Dietrich (Fortschr. Kieferorthop. 42 (1981), 195-208) demonstrates itself in a lack of torque strength, slit deformation and abrasion or in the breaking of the wing of the brackets, as well as the occurrence of high friction in the slit.

Even if a metal insert is built into the slit, such as, for example, according to DE No. 2,742,896, these disadvantages are only incompletely removed.

Brackets made of ceramic, preferably of $Al_2O_3$, as described in DE-OS No. 2,913,509 and the U.S. Pat. No. 4,219,617, combine an aesthetically favorable effect and good mechanical strength and, therefore, are superior to metal or synthetic resin brackets. The manufacture of ceramic brackets, however, proves to be expensive and problematic because, among others, of the uncontrollably occurring shrinkage during the vitrifying process which absolutely necessitates mechanical after-treatment which, however, can only be realized by means of diamond tools. Furthermore, an individual adaptation of the base surface of the ceramic braces to the shape of the tooth, which is required in certain cases, is only possible with difficulty, because the ceramic is only poorly machine due to its structure and the contained crystal phases. It is a further disadvantage of ceramic brackets that in order to attain sufficient bonding strengths, there are required indentations in the base surface of the brackets in order to assure better adhesion of the orthdontic adhesive, which leads to an additional expenditure in the production of the ceramic adhesive brackets.

The use of $Al_2O_3$ ceramic or glass ceramic as implant material is known in head and neck surgery. Because of the chemical material composition of their precipitated crystal phases and their structure, these known glass ceramic materials have the disadvantage that they are difficult to work on intraoperatively.

According to DE-OS No. 3,211,211 and DE-OS No. 3,211,209 there is known, furthermore, a combination of bioinert and bioactive materials for prostheses of the auditory ossicle. The disadvantage of this technical solution consists in that, because of the material strength and its bioinert surface coating, it cannot be worked on intraoperatively.

Furthermore, the operating surgeon has to have available a large assortment of various implant bodies corresponding to the anatomical conditions.

Another disadvantage of this known combination in the category of utilization of generally known glass ceramics is that the partial components have different thermal expansion coefficients so that, in particular, during sterilization, there can occur structural damages on the bonding locations. Especially in large-area implant bodies, the different thermal expansion coefficients of the partial components have a disadvantageous effect.

SUMMARY OF THE INVENTION

An object of the invention is to provide a glass ceramic which in respect to the material, as compared to the state of art known up to now, makes possible properties which open up completely new fields of application, in particular for medical purposes, preferably in stomatology and head surgery and neck surgery.

Another object of the invention is to develop a glass ceramic which is excellently machineable with conventional hard metal tools and which, at the same time, possesses a high fracture bending strength and hardness, as well as further adjustable properties according to the application purposes, whereby the preferable task of the invention, furthermore, consists in that 1. with respect to the application of the glass ceramic in stomatology
   the glass ceramic is well tolerated biologically,
   the up to now existing differences of expansion between tooth and artificial dental material are to be reduced to a minimum,
   the hardness and strength which were too low in the up to now used dental materials are overcome,
   a material is to be used which has an aesthetically better or adapted color effect,
   the up to now used very expensive precious metals or alloys are to be replaced by the use of the new material on an economically advantageous raw material basis,
   the usual simple primary shaping and recasting techniques of glass technology are to be used for an economically advantageous manufacturing process;
2. furthermore, with respect to the application of the glass ceramic for veneer laminates
   a simple adaptation and bonding of the glass ceramic to a tooth made of synthetic resin, a metal frame or a natural tooth is possible,
   industrial manufacturing methods can be used;
3. furthermore, with respect to the application of the glass ceramic in dental orthopedics/orthodontics
   the glass ceramic possesses a high retention capacity with respect to orthodontic adhesives;
4. furthermore, with respect to the application of the glass ceramic in head surgery and neck surgery
   the glass ceramic can be worked on intraoperatively with the conventional instruments which are available during surgery so that the implant body can be adapted to an optimum to individually very different anatomical conditions,
   a combination of the glass ceramic with a highly bioactive glass ceramic is possible.

The object of the invention is solved in that the glass ceramic has a composition in weight-% in the narrow limits of

| | |
|---|---|
| $SiO_2$ | 43–50 |
| $Al_2O_3$ | 26–30 |
| MgO | 11–15 |
| $R_2O$ | 7–10.5 |
| $F^-$ | 3.3–4.8 |
| $Cl^-$ | 0.01–0.6 |
| CaO | 0.1–3 |
| $P_2O_5$ | 0.1–5 | wherein $R_2O$ is the sum of 3 to 5.5 wt-% $Na_2O$ and 4 to 6 wt-% $K_2O$, and as crystal phases contains mica in addition to 5 to 30 wt-% cordierite, whereby the structure is characterized in that relatively large, preferably bent, mica crystals of a size of 10–200 μm are present embedded in the glass matrix and cordierite crystals of a size of 0.5 to 5 μm are arranged, whereby smaller, flat mica of a size of 0.5 to 5 μm can also occur.

In order to improve the physical and chemical properties, the micaceous-cordierite-glass ceramic can also contain the additional components BaO, SrO and PbO of up to 8 wt-% or for the color configuration color components, such as, for example, NiO, $Cr_2O_3$, $MnO_2$, FeO, $Fe_2O_3$ and $TiO_2$ at 4 wt-% individually or in a mixture.

BRIEF DESCRIPTION OF THE DRAWINGS

The invention will be better understood by reference to the accompanying drawings, in which.

DETAILED DESCRIPTION OF THE PREFERRED EMBODIMENTS

It was surprising that the disadvantageous properties of glass ceramics, which alone contain only large bent mica crystals or crystal phases, were overcome in that by means of an international double crystallization of the initial glass, it is possible to precipitate in addition to large bent mica crystals simultaneously also small flat mica crystals and/or a second crystal phase, which represents cordierite, between the large bent mica crystals.

The formation of the cordierite crystal phase in the glass ceramic has been clearly proven by evaluation of X-ray diffraction examinations and scanning electron microscopic examinations.

This double controlled crystallization is successful in the in itself known $SiO_2-Al_2O_3-MgO-Na_2O-K_2O-F^-$ system, however, only if the narrow range of composition according to the invention of the components $SiO_2$, $Al_2O_3$, $MgO$, $Na_2O$, $K_2O$, $F^-$ is selected and the glass ceramic according to the invention at the same time contains 0.01 to 0.6 wt-% $Cl^-$, 0.1 to 3 wt-% $CaO$ and 0.1 to 5 wt-% $P_2O_5$. This relatively narrow range of composition according to the invention is a basic condition in order that the microphase formation processes in the initial glass, which are necessary for an intentional double controlled crystallization, can occur. It is characteristic thereby that the initial glass consists of a drop-shaped glass phase and a glassy matrix phase. This has been clearly proven in the electron microscopic image. The drop-glass phase represents a silicate phase rich in $Mg^{2+}$, $Na^+$, $K^+$, $Al^{3+}$, the glass matrix is rich in $SiO_2$. Out of the drop-glass phase, during the process of the thermal after-treatment are formed the bent mica crystals which, as is known, are richer in $Al^{3+}$ than the flat mica crystals (Hoeland, Vogel et al., Glass Technology 24 (1983) 318). With continuing crystallization, there therefore occurs an impoverishment of $Al^{3+}$ ions, but also of $Mg^{2+}$, $Na^+$, $K^+$, $F^-$ ions and (of course) $SiO_2$ in the residual glass so that, at first, there "just barely" occur platelet-like mica crystals, and at a further impoverishment of the glass phase mainly of $Na^+$ and $K^+$ ions, there occurs an intentional cordierite crystallization. Thus, the diffusion processes decisive for the crystallization are exactly controllable by means of the various stages of the thermal treatment so that the control of the course of the different formation of the crystal phases and the fixation of the portions of the crystal phases is possible.

The addition of the components $BaO$, $SrO$ and $PbO$ of up to 8 wt-%, as well as the addition of the color components, such as, for instance, $NiO$, $Cr_2O_3$, $MnO_2$, $FeO$, $Fe_2O_3$, $TiO_2$ of up to 4 wt-% individually or in mixture, gives the material new additional desired colors, different degrees of opacity or also fluorescence.

The production of the initial glass can also occur according to the primary shaping methods known in glass technology, such as, for example, casting, pressing, centrifuging or drawing into an object. The object is subsequently cooled down to room temperature or converted directly in the range of 600°–1050° C. into the glass ceramic according to the invention. During this in-situ crystallization of the initial glass, it is advantageous that the object is embedded, or even covered, in a mold (for example metal or ceramic material). Thus is made possible the production of objects with very complicated external shapes without the occurrence of even the slightest deformations.

The resulting glass ceramic according to the invention has the particular combination of properties of excellent machineability, a high fracture toughness of up to 2.0 MPa m$^{\frac{1}{2}}$, a hardness as $HV_{0.07}$ to 1000, a compressive strength of up to 450 N/mm$^2$, an adjustable linear thermal expansion coefficient of 75 to $125 \times 10^{-7} K^{-1}$ and a good chemical stability, as well as a high resistance to abrasion.

This enormous progress in the combination of the properties attained in comparison to the state of art which has become known up to now is brought about by simultaneous precipitation of large bent mica crystals and small flat mica crystals and/or small cordierite crystals in the glass ceramic according to the invention. The formation of micro stresses by means of the precipitated crystal phases causes thereby the decisive effect for the intentional variations of the properties and for the thereof resulting new fields of application, preferably in medicine.

In regard to the production of specific properties, such as, for example, high strength, adjustable expansion coefficients, biological compatibility, etc., it was surprising that in addition to attaining the excellent machineability properties, that micaceous-cordierite-glass ceramics can be used for stomatological purposes. This surprising useful effect is based on the fact that better mechanical, thermal and processing properties or overall new physical properties and chemical properties have been created in mica-cordierite-glass ceramics than existed in known biomaterials or known micaceous glass ceramics.

To begin with, good chemical properties, such as hydrolytic stability of micaceous glass ceramics are known. It was surprising, however, to be able to prove for the products according to the invention that the glass ceramics are biocompatible in the biological environment, for example, in the cavity of the mouth of humans. The surprisingly proven new physical properties of the micaceous-cordierite-glass ceramics are, for instance, the linear thermal expansion coefficient which can be varied up to $125 \times 10^{-7} K^{-1}$, the mechanical strength and hardness, the abrasion of the materials and the processing properties of the initial glass for the manufacturing of the glass ceramic up to the process of the ceramification and the possibility of combining it with high-strength materials.

According to the invention micaceous-cordierite-glass ceramics can be used in stomatology, preferably for inlays, crowns, structures and bridges of any shape. In order to maintain the optimum mechanical parameters in these applications, however, a minimum wall thickness of 0.5 mm is advantageous.

Tooth enamel (natural tooth), for example, has a linear thermal expansion coefficient of $114 \times 10^{-7} K^{-1}$. Micaceous-cordierite-glass ceramic consists of an up to now unknown structure, i.e., of large bent and small flat fluoroplogopite crystals and/or cordierite crystals which are highly cross-linking. Thus, these materials have an expansion coefficient which can be directly adjusted to that of tooth enamel, and a utilization for dental restoration, for example, for inlays, crowns, tooth structures and bridges is possible according to the invention. Thus has been achieved a considerable progress in reference to the state of art, because it is possible to avoid uncontrolled stress and the formation of peripheral cracks between the biomaterial and the tooth, and a long-term functioning period for dental products in the lateral tooth area is attained.

The variability in the adjustment of the expansion coefficient is simultaneously a prerequisite for combinations of the glass ceramic with high-strength materials, such as, for example, a compound material made of an Al₂O₃ and micaceous-cordierite-glass ceramic for a tooth structure or bridge construction.

Very good strengths and hardness parameters are known for micaceous-glass ceramics. For the application in stomatology, such as, preferably, for inlays, crowns, tooth structures and bridges, a multitude of mechanical parameters have to attain optimum values in comparison to tooth enamel. Thus, it was surprising to find that the abrasion behavior of micaceous-cordierite-glass ceramics is similar to those of natural tooth enamel. Simultaneously, the materials have a hardness of 300–800 ($HV_{0.07}$), fracture bending strengths of more than 80 MPa (value of the lower limit), compressive strengths of up to 450 N/mm², and a roughness depth of 0.15 μm and a very good chemical stability, in accordance, for example, with the hydrolytic class 1 and 2 according to TGL 14809 or RGW Standard 1569. The materials, at the same time, have an excellent machining property, so that utilization for the dental products made of glass ceramic, as stated in the examples, has become possible. Furthermore, measured by the fracture bending strength, in comparison to tetrasilicic-acid-mica-glass ceramic described in U.S. Pat. No. 4,431,420, a considerable progress has been achieved, because the latter material broke at a lower limit of approximately 50 MPa.

In comparison to precious metals, the progress attained with the application of the cordierite-micaceous-glass ceramic according to the invention for stomatological purposes, moreover, is obvious. Firstly, because of the tooth-like appearance of the glass ceramic as compared to a crown made of precious metal, there is already attained a considerably improved cosmetic effect. The main efficacy, however, is attained in the economical area due to the considerably less expensive raw materials. Simultaneously, the main properties of the glass ceramic are considerably more similar to tooth enamel than the main properties of metals (for example, heat conductivity, expansion, abrasion, mechanical properties). Especially advantageous is also that in relation to known methods for the production of vitrified ceramics inlays, crowns, structures, bridges, etc., made of micaceous-cordierite-glass ceramic, can be produced according to known primary shaping and reshaping methods, such as, for example, pressing, centrifuging and casting.

Consequently, it is possible to produce according to requirements, i.e., depending on the anatomical particularity, desired optional shapes, for instance, of inlays and crowns or structures and bridges. Individually, the production method consists in that an initial glass in the form of glass-frit or compact material is melted at 1450° to 1530° C. and at a temperature of approximately 1250°–1350° C., which corresponds to a viscosity of the glass of $10^1$ to $10^2$ Pas, is cast in a muffle which has been preformed according to a desired tooth restoration and has been preheated to a temperature of 500°–1000° C.

The muffle consists of embedding masses which are conventionally used in dental laboratories, for instance, for the model cast of prostheses made of chromium-cobalt-molybdenum alloys and chromium-nickel alloys, as well as steel. The casting duct of the muffle should not be any longer than 10 mm and its diameter should be at least 2–3 mm. In order to provide better air-relief, the muffle can also be provided an air-relief duct which normally, however, is not necessary. During casting, the complete charging of the glass into the preformed muffle for the production of the particular shaped body is attained by means of a centrifuging method or by applying vacuum.

The shaped body can then be cooled to room temperature inside of the muffle or can be converted directly at a temperature range of 650° C. to 1050° C. in 0.5 to 24 hours into a glass ceramic. In both cases, a single or multiple-step thermal treatment is possible. If the muffle is cooled to room temperature immediately after the primary shaping process, it allows after removal from the embedding a visual examination of the glass body with respect to possibly occurring flaws in the primary shaping process (for example, chips, cracks, blisters, incompletely filled mold) and segregation of flawed glass bodies. If the glass body is flawless, it is heated with 10 K/min to a temperature of 600°–1000° C. and thus converted into the dental products made of glass ceramic according to the invention. This thermal treatment will be referred to hereinafter as the ceramification process. In order to ensure the uniformity of shape, it is advantageous to embed the glass bodies again before ceramification. After the ceramification process, the glass-ceramic parts are removed from the embedding and freed from adhering embedding mass by means of processing with conventional dentistry tools or also by means of blasting with fine-grained sand. By means of grinding and polishing are achieved external surfaces of optimum smoothness and shine which surfaces have a roughness depth of up to 0.15 μm.

According to the same method steps as mentioned for the production of solid micaceous-cordierite-glass ceramics for stomatological purposes, it is possible to produce compound materials made of a high-strength base body, for example, Al₂O₃ vitrified ceramic and the micaceous-cordierite-glass ceramic, whereby the base body is either entirely or partially enclosed. In this case, the base body is already inserted in the model, which is made, for example, of wax. The resulting dental products according to the invention, for example, bridges or structures, have strengths of 200–400 MPa.

Another positive effect results in that conventional ceramic pigments and/or glazes can be applied to the dental products made of glass-ceramics according to the invention. Thus is made possible an individualized pigmentation.

A similar individual pigmentation of the micaceous-cordierite-glass ceramics has been achieved in that the additional components SrO, BaO, PbO of up to 8 wt-% and the color components FeO, $Fe_2O_3$, $MnO_2$, NiO, $Cr_2O_3$, $TiO_2$ of up to 4 wt-% cause a pigmentation, but surprisingly do not essentially influence the phase formation process. Another advantage of the utilization of micaceous-cordierite-glass ceramics for stomatological purposes consists in that due to the excellent machineability, production can be accomplished by milling and/or drilling and/or turning and/or sawing and/or grinding without requiring diamond tools.

According to the invention the application of micaceous-cordierite-glass ceramic for veneer laminates is solved in that the veneer shell consists vestibularily of a glass ceramic layer and orally of an organic synthetic resin layer or compound material layer, whereby the two layers are connected to each other by means of a layer which facilitates cohesion and whereby, furthermore, not only the advantageous machineability features but also the good physical and chemical properties, the aesthetic configuration options and pigmentation of the glass ceramic are utilized at an optimum. Thus it is possible to produce veneer laminates of low thickness, whereby the glass ceramic layer can be produced by casting methods or pressing methods which are known in glass technology. Thus is provided an industrial manufacturing possibility of the mentioned veneer laminates. The individual imparting of pigmentation to the veneer laminate is realized in addition to the tooth-colored glass ceramic layer by means of a tooth-colored organic artificial material layer or compound material layer.

The vestibulary glass ceramic layer according to the invention permits a reduction of the thickness of the layer to an outer layer of equal to or less than 0.5 mm which, similarly to the dental enamel of the natural tooth, guarantees the biocompatibility of the veneer laminate, ensures the optical properties and, as part of the compound body, allows the organic synthetic resin layer or compound material layer to be made equal to or thicker than 1 mm. Thus the individual adaptation of an industrially produced facing laminate can take place exclusively in the area of the organic synthetic resin layer or compound material layer without touching the layer which facilitates cohesion. Simulatneously, the oral backing of the glass ceramic layer with organic synthetic resin or compound material allows a simple adaptation and coupling to the body which has to be provided with a facing. The application of the adhesive-facilitator layer takes place in a known way by utilizing silicon-organic compounds, for example, tetraethoxysilane. A relatively enlarged surface structure in relation to the geometric surface contributes to the improvement of the adhesive properties; the enlarged surface structure is produced by appropriate configuration of the metal compression mold on the oral side of the vestibulary glass ceramic layer and is reinforced by subsequent conditioning methods. For an additional application of the micaceous-cordierite-glass ceramic according to the invention in dental orthopedics/orthodontics, preferably for adhesive brackets and small adhesive buttons, it is of great importance, that already during the production of the initial glass, it is possible to perform an extensive preshaping of the adhesive brackets and small adhesive buttons by means of known primary shaping methods, such as, for example, casting or pressing.

Because of the excellent machineability of micaceous-cordierite-glass ceramic, the final finishing of the parts can be performed by means of working with conventional hard metal tools, whereby this process can be carried out, on the one hand, by the production of standardized base bodies and, on the other hand, by automation, and thus an economically advantageous way.

A required individual adaptation of the base surface of the adhesive brackets to the shape of the tooth is also assured because of the excellent machineability of the micaceous-cordierite-glass ceramic, for example, by grinding with the conventional grinding bodies of dentistry and represents a considerable progress in relation to the ceramic brackets described in DE-OS No. 2,913,509 and U.S. Pat. No. 4,219,617.

In comparison to metal brackets which require expensive methods in order to attain a micromechanical retention surface for orthodontal adhesives or in comparison to ceramic brackets which require the creation of additional retention cavities, in micaceous-cordierite-glass ceramic brackets, there is attained an excellent micromechanical retention surface already by means of a simple precision grinding of the base surface, whereby there are attained considerably higher bonding strength values than in adhesive metal or ceramic brackets. Additionally advantageous for the bonding strength between adhesive brackets made of glass ceramic and tooth enamel is the possibility of being able to adjust the linear thermal expansion coefficent of the micaceous-cordierite-glass ceramic to the value of the tooth enamel and thus to be able to avoid stresses occurring due to temperature fluctuations.

Furthermore, the excellent physical and chemical properties of the micaceous-cordierite-glass ceramic, as well as its good biological compatibility and stability in the environment of the mouth is of great importance for the application in dental orthopedics/orthodontics.

The tooth-colored appearance of the micaceous-cordierite-glass ceramic, which can be additionally improved by means of additive coloring components, has a very favorable effect for the patient from a cosmetic point of view, whereby is essential that in contrast to brackets made of synthetic resin there do not occur any permanent and disadvantageous discolorations, for example, due to foodstuff or coffee, tea and cigarettes, etc. Furthermore, adhesive brackets made of glass ceramic according to the invention excel in that they have pleasant wearing properties for the patient due to their configuration and because the edges of the adhesive brackets made of glass ceramic are broken or rounded off.

According to the invention, the implant material for head and neck surgery consists only of micaceous-cordierite-glass ceramic or of a combination of a highly bioactive glass ceramic with machining properties and the mentioned biocompatible micaceous-cordierite-glass ceramic. The highly bioactive glass ceramic with machining properties has the following composition in weight percentages (DE-OS No. 3,306,648):

| | |
|---|---|
| $SiO_2$ | 19–52 |
| $Al_2O_3$ | 12–23 |
| $MgO$ | 5–15 |
| $Na_2O/K_2O$ | 3–10 |
| $CaO$ | 9–30 |
| $P_2O_5$ | 4–24 |
| $F^-$ | 0.5–7 |

The combination of the indicated biocompatible micaceous-cordierite-glass ceramic and the highly bioactive glass ceramic is advantageous because in the softening phase, due to accordingly adjusted linear thermal expansion coefficients, they are tightly connected to one another and, consequently, there cannot occur any structural disruptions at the phase boundaries during temperature changes.

For the processing of the glass ceramic combination the distinguishing marking of the phase boundary between the highly bioactive glass ceramic and the mentioned micaceous-cordierite-glass ceramic is important. It occurs in that the phase boundary between the two glass ceramics which are to be connected is made visible as a colored boundary layer in that small quantities of color oxides are added before the thermal treatment of the initial products.

The utilization of the micaceous-cordierite-glass ceramic according to the invention has the advantage of a low solubility which guarantees a long-term shape constancy. Furthermore, it has a high surface charge which causes in the area of the ears, the nose and the paranasal sinuses as well as in the trachea a quick secondary epithelization. Overall, the utilization of the mentioned glass ceramic according to the invention has the advantage that it can be worked on intraoperatively with the conventional instruments which are available during the operation. Furthermore, good blood tolerance of the micaceous-cordierite-glass ceramic according to the invention makes possible its utilization in the cardiovascular system, for example, for heart pumps.

The invention will be explained hereinafter in greater detail by means of the exemplified embodiments. Table 1 shows a summary of the chemical composition in weight % of the glass ceramics or the initial glasses thereof according to the invention. Table 2 gives examples which show the connection between chemical composition, thermal treatment of the initial glasses, composition of crystal phases and properties of the glass ceramics according to the invention. A multitude of possible property combinations of the glass ceramics according to the invention exist, such as, for example, a high fracture toughness with good to very good machining properties at a linear thermal expansion coefficient which can be adjusted within a wide range of limits or high hardness with a good machining property at a simultaneously very good chemical stability.

(1) and as tooth structure (2) illustrate the useful effect of the application according to the invention:

(1) For the production of an inlay made of micaceous-cordierite-glass ceramic, at first, there takes place the preparation of the tooth cavity. Thereby has to be paid attention to the arrangement that the perpendicularly mating surfaces of the walls of the cavities have slightly rounded edges. Thin, runny preparations have to be avoided. A sufficiently large substance excavation, which provides for a layer thicknesses of at least 1.0 mm, in case of inlays, is to be aimed for. The production of the model which is intended for the embedding, and which reflects the extent and shape of the cavity, can be carried out according to the direct method, for example, by modelling wax in the mouth, or according to the indirect method, for example, via an impression and production of a special stump. After completion of the model is attached a casting pin which has a length of 5 to 10 mm and a diameter of 2–3 mm. The embedding occurs by using embedding masses, as conventionally used in dental laboratories for casting high-melting dental alloys. Advantageous is the utilization of a vacu-

TABLE 1

| Compositions of micaceous-cordierite-glass ceramic or initial glasses thereof | | | | | | | | | | | |
|---|---|---|---|---|---|---|---|---|---|---|---|
| | 1 | 2 | 3 | 4 | 5 | 6 | 7 | 8 | 9 | 10 | 11 |
| $SiO_2$ | 45.2 | 47.3 | 49.3 | 43.6 | 44.1 | 45.3 | 45.0 | 42.9 | 45.3 | 45.0 | 44.6 |
| $Al_2O_3$ | 29.6 | 25.7 | 26.4 | 26.3 | 27.6 | 28.1 | 25.9 | 26.0 | 26.3 | 28.5 | 26.9 |
| $MgO$ | 12.0 | 11.1 | 11.8 | 14.7 | 11.4 | 13.6 | 11.1 | 11.9 | 11.5 | 11.9 | 12.3 |
| $Na_2O$ | 3.9 | 3.1 | 3.3 | 5.2 | 4.2 | 4.3 | 3.3 | 3.0 | 3.2 | 3.7 | 3.5 |
| $K_2O$ | 4.5 | 4.8 | 4.0 | 4.3 | 5.8 | 4.8 | 5.1 | 3.8 | 4.6 | 4.3 | 4.6 |
| $F^-$ | 4.2 | 3.5 | 4.1 | 4.5 | 3.9 | 3.3 | 4.2 | 4.2 | 4.0 | 4.2 | 4.1 |
| $Cl^-$ | 0.1 | 0.05 | 0.5 | 0.2 | 0.1 | 0.4 | 0.1 | 0.05 | 0.3 | 0.05 | 0.1 |
| $CaO$ | 0.1 | 0.5 | 0.3 | 0.1 | 2.8 | 0.1 | 0.3 | 0.1 | 0.1 | 0.1 | 0.1 |
| $P_2O_5$ | 0.3 | 4.0 | 0.2 | 1.1 | 0.1 | 0.1 | 0.5 | 0.2 | 0.7 | 0.1 | 0.3 |
| $SrO$ | — | — | — | — | — | — | 4.5 | — | — | — | — |
| $PbO$ | — | — | — | — | — | — | — | 7.9 | — | — | — |
| $Fe_2O_3$ | — | — | — | — | — | — | — | — | 3.7 | — | — |
| $MnO_2$ | — | — | — | — | — | — | — | — | — | 2.2 | — |
| $TiO_2$ | — | — | — | — | — | — | — | — | 0.2 | — | 3.5 |

TABLE 2

| Thermal treatment of the glassy products and properties of the resulting micaceous-cordierite-glass ceramics | | | | | | | | |
|---|---|---|---|---|---|---|---|---|
| Thermal treatment or properties | 1 | 1 | 2 | 4 | 6 | 8 | 10 | 11 |
| temperature (°C.) | 650/960 | 680/1020 | 930 | 980 | 830 | 1020 | 850 | 630/990 |
| tempering time (h) | 1/3 | 1/2/3/2 | 5 | 3/2 | 50 | 1/2 | 30 | 1/2/3 |
| fracture bending strength (MPa) | 90 | 150 | 95 | 100 | 105 | 145 | 125 | 115 |
| fracture toughness $K_{IC}$ (MPa m$^{\frac{1}{2}}$) | 1 2 | 1 9 | — | 1 3 | — | 1 7 | 1 5 | — |
| hardness $HV_{0.07}$ | 300 | 420 | — | — | 750 | — | 980 | — |
| compressive strength (MPa) | 280 | — | 310 | — | 420 | — | 455 | — |
| linear thermal expansion coefficient ($K^{-1}$) | $108.10^{-7}$ | $115.10^{-7}$ | $77.10^{-7}$ | $122.10^{-7}$ | $93.10^{-7}$ | — | $112.10^{-7}$ | — |
| machining property | very good | good | good | very good | good | good | good | very good |
| hydrolytic class | 2 | 1-2 | — | 2 | 1 | — | 1 | 2 |
| color | white | white | white | white | white | white | brownish | gray/brownish |
| resistance to abrasion | good | — | good | — | very good | very good | very good | — |
| depth of roughness (μm) | 0.25 | — | — | — | 0.15 | — | 0.15 | — |
| portion of crystal phases (Vol-%) | | | | | | | | |
| mica | 65 | 65 | 60 | 60 | 45 | 50 | 60 | 70 |
| cordierite | 5 | 5 | 15 | 10 | 30 | 10 | 15 | 5 |

The examples reported in tables 1 and 2 also provide evidence for the advantageous application of the micaceous-cordierite-glass ceramic according to the invention for stomatological purposes.

Two further selected examples, i.e., for the application of the micaceous-cordierite-glass ceramic as inlay um-vibration instrument, such as is usually available in dental laboratories.

When the embedding mass has hardened, the casting pin is removed and the muffle is slowly preheated to a temperature of 500°–1000° C. During this process the model material escapes through the casting duct and leaves in the muffle a cavity corresponding to its original shape. The initial glass is melted at 1450°–1530° C. and cast at a temperature of approximately 1250°–1350° C. by means of the centrifuging method or vacuum-pressure casting in the muffle, whereby the mentioned cavity fills up. As the product of the casting method, the glass ceramic inlay can now be cooled down to room temperature in the muffle. Subsequently, by removal from the embedding, it is freed of the surrounding embedding mass and examined for possible flaws. If the cast object is free of flaws, it is embedded again, thereby an embedding mass of the same composition as was used in casting is used. By heating with 10 K/min to a temperature of 650°–1050° C. over a time period of 0.5–24 hours takes place a ceramification into the glass ceramic inlay according to the invention. The inlay is subsequently removed from the embedding. An additional possibility consists in the conversion of the casting process into the ceramification process, which also takes place at a temperature of 650°–1050° C. without intermediary removal of the casting object from the embedding. In order to remove the residues of adhering embedding mass, the inlay is blasted with quartz sand. The inlay is separated from the casting duct by means of a conventional grinder. At this point, the inlay can be tested for fit in the mouth. The fitting capability is controlled, for example, peripheral closure, contact points with the adjacent teeth, occlusion, corrections are carried out with fine-grained grinders. Subsequently takes place the polishing in the conventional way. If necessary, for example, in case of insertion in a visible area, an extensive adaptation to the pigmentation of the natural teeth takes place by applying pigments or burning-in the pigments or by previous addition of additional components. Finally, the inlay is anchored in the cavity with the conventional fastening cements of dental praxis or special adhesion methods.

(2) For the production of a tooth structure made of micaceous-cordierite-glass ceramic in combination with $Al_2O_3$ vitrified ceramics, there is at first carried out the excavation of the tooth and hollowing of the root canal. Then occurs the fitting of a ready-made root pin made of $Al_2O_3$ reinforced ceramic. The pin has, for example, a round cross-section, and is provided in various thicknesses according to the widths of the root canal, for example, of a cross-section of 1.4 mm, 1.6 mm, 1.8 mm, and is slightly tapered towards the tip of the root. The length of the pin has to be adapted to the course of the root canal by means of grinding. The actual structure of the tooth corresponds in its configuration to a preparation stump and is modelled of modelling material according to the direct method. The work steps from the embedding to the ceramification process correspond to the same explanations for (1) above. In order to test the fitting property, the ceramic tooth structure is fitted on the patient. Attention is given to peripheral closure behavior, length and correct shape. The work on the surface is carried out with the conventional grinding and polishing bodies of dental praxis. The cementing in place corresponds to that explained in (1) above occurring after correct root filling in the apical third.

Figure 1:
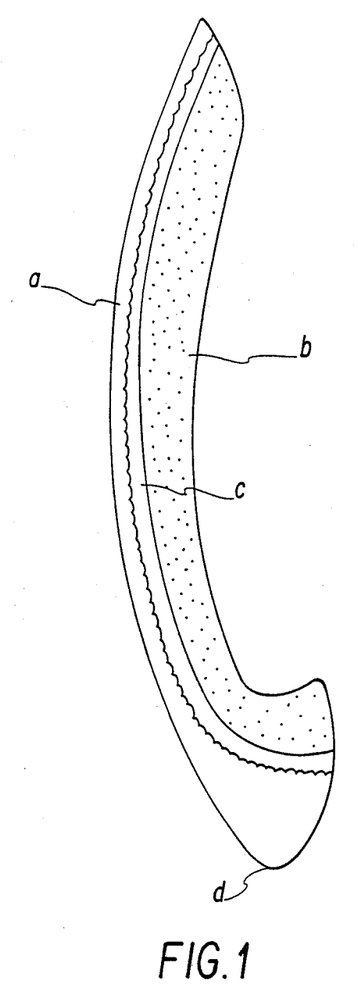
FIG. 1 is a side vestibulary-oral cross-sectional view of a veneer laminates for a tooth employing the micaceous-cordierite-glass ceramic of the present invention.
Figure 2:
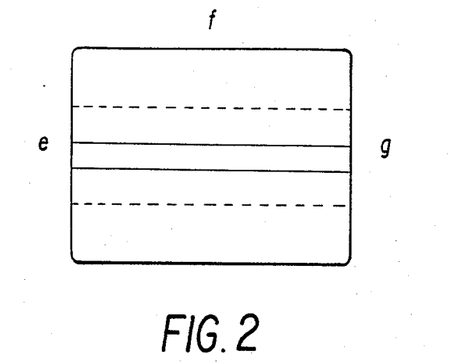
FIG. 2 is a top plan view of an embodiment of an adhesive glass ceramic orthopedic/orthodontic brackets employing the micaceous-cordierite-glass ceramic of the present invention.

The nature of the invention with regard to the application of the micaceous-cordierite-glass ceramic for veneer laminates will be more closely explained hereinafter by means of an exemplified embodiment. In FIG. 1 is a vestibulary-oral cross-section of the a veneer bracket according to the invention. The veneer shell according to the invention consists of a vestibulary glass-ceramic layer a, an adhesion-facilitator layer b and an organic synthetic resin layer or compound material layer c. The glass ceramic layer a therein consists of a micaceous-cordierite-glass ceramic of the composition according to the nature of the invention. It is pressed by means of metallic molds, ceramified and surface-conditioned. The conditioning of the surface occurs by means of sand-blasting with $Al_2O_3$ corundum of a grain size of 50 μm and 2–3 bar pressure.

Subsequently, a cleaning with ethyl acetate takes place in an ultrasonic bath. The labial or buccal surface of the vestibulary glass ceramic layer is provided with the surface configuration of the particular tooth which it represents. The incisal edge d is of such configuration that it extends in the lingual direction without any differentiation. On the lingual surface of the vestibulary glass ceramic layer a is applied the adhesion-facilitator layer b by means of silanizing. Subsequently, the organic synthetic resin layer or compound material layer c is applied on the adhesion-facilitator layer b and thus the vestibulary glass ceramic layer a is orally backed. Thereby is at first applied highly cross-linking synthetic resin layer which is complemented with a highly-filled, pigment-carrying pasty phase of a bonding substance. Both layers contain photoinitiators and are simultaneously light-polymerized.

The application of the micaceous-cordierite-glass ceramic according to the invention in dental orthopedics/orthodontics will be further explained hereinafter by means of two exemplified embodiments.

Figure 3:
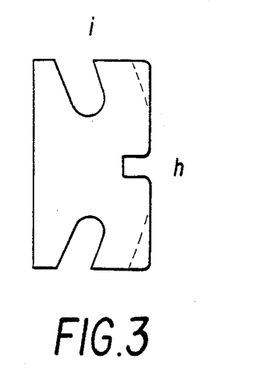
FIG. 3 is a side plan view of the brackets shown in FIG. 2.
Figure 4:
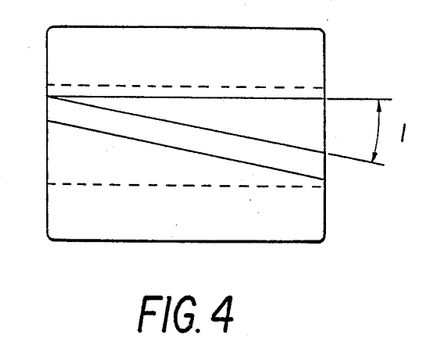
FIG. 4 is a top plan view of a second embodiment of an adhesive glass ceramic orthopedic/orthodontic brackets employing the micaceous-cordierite-glass ceramic of the present invention.
Figure 5:
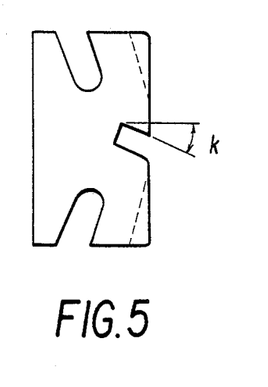
FIG. 5 is a side plan view of the brackets shown in FIG. 4.

FIGS. 2, 3, 4 and 5 show various views or possibilities for the shape of adhesive glass ceramic bracket, whereby the glass ceramic essentially has the indicated composition and properties of the invention. The base surface of the bracket has an end length e of 4.5 mm and f of 2.5 to 6 mm and is of an arched or flat configuration and by grinding with conventional grinding means is provided with a micromechanical retention surface for orthodontic adhesives in order to attain adhesion strengths of up to 18 MPa. The height i of the brackets is at a maximum 3 mm and the wings according to FIGS. 3 and 4 are straight or bevelled, whereby the edges of the adhesive micaceous-cordierite-glass ceramic brackets are broken or rounded off. The slit of the adhesive glass ceramic brackets for receiving the adjustment arch has a width g of 0.45 to 0.55 mm and a depth h of 0.6 to 0.7 mm. The angulation of the slit, the angle 1 in FIG. 4, can amount up to 10° and the torque of the slit, the angle k in FIG. 5, can amount to as much as 25°. According to the indications for the shape, there can be produced standardized base bodies for the different types of teeth.

After individual fitting of the standardized adhesive glass ceramic brackets and after conditioning of the dental enamel, the adhesive glass ceramic brackets are fastened on the teeth by means of orthodontic adhesives, such as, for instance, polymethylmetacrylate, and the correction of the anomalies of the positions of the teeth occurs by means of the retention of highly-elastic adjustment arches.

Figure 6:
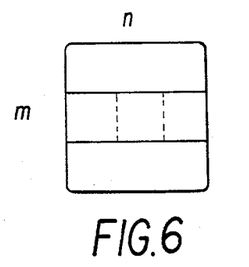
FIG. 6 is a top plan view of one embodiment of an adhesive micaceous-cordierite-glass ceramic button acording to the present invention.
Figure 7:
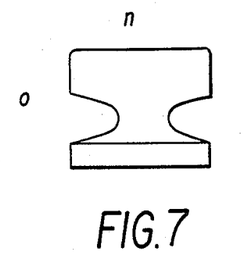
FIG. 7 is a side plan view of the button shown in FIG. 7.
Figure 8:
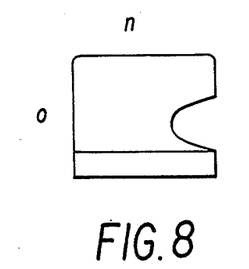
FIG. 8 is a side plan view of a second embodiment of an adjesive micaceous-cordierite-glass ceramic button according to the present invention.

FIGS. 6, 7 and 8 show different views or possibilities of the shape of small adhesive glass ceramic buttons, whereby in the FIGS. 6 and 7 the structure on the base surface has a T-shape and in FIG. 8 a hook-shape. The edges of the small adhesive glass ceramic buttons are also broken or rounded off and the edges m and n of the base surface are 2.5–3 mm long and the height o is a maximum of 3 mm. The small adhesive micaceous-cordierite-glass ceramic buttons are fastened on the teeth, as described in the first exemplified embodiment and serve, for example, for receiving the elastic traction.

The application of the micaceous-cordierite-glass ceramic according to the invention for implant material in head surgery and neck surgery will be further explained hereinafter in two exemplified embodiments.

Figure 9:
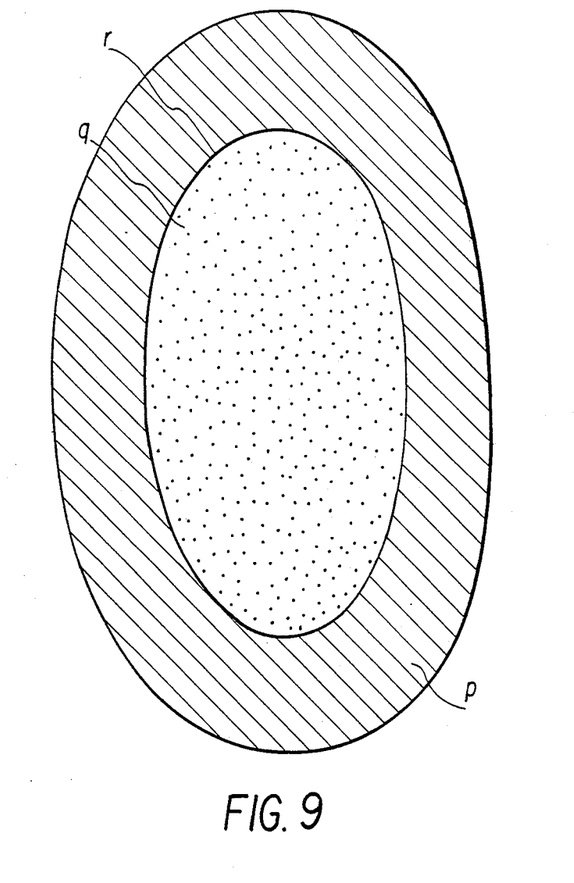
FIG. 9 is a cross-sectional view of an implant body for surgery of the paranasal sinuses, having a bioactive peripheral bone and employing the micaceous-cordierite-glass ceramic of the present invention.

The implant body for surgery of the paranasal sinuses shown in FIG. 9 consists of a bioactive pheripheral zone p and a biocompatible micaceous-cordierite-glass ceramic core zone q. The peripheral zone p and the core zone q are visibly marked at their phase boundary r by means of adding color oxides, such as, for example, $FeO/Fe_2O_3$, $MnO_2$, $Cr_2O_3$ or NiO. The surface configuration can be flat or bent in accordance with the anatomical conditions.

The version of the pheripheral zone p made of highly bioactive glass ceramic guarantees a strong bond with the bone. The core zone q facilitates the epithelization based on the properties of the utilized biocompatible micaceous-cordierite-glass ceramic.

Figure 10:
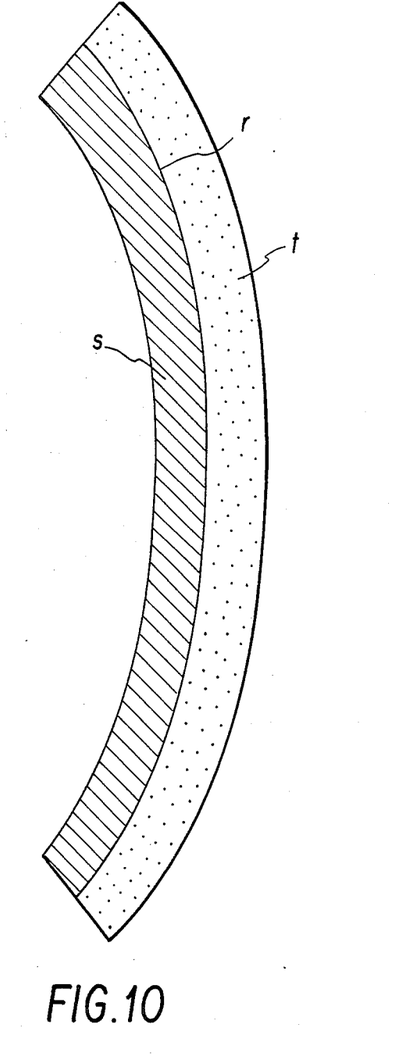
FIG. 10 is a cross-sectional view of an implant body for surgery of the paranasal sinuses, having a bioactive surface layer and employing the micaceous-cordierite-glass ceramic of the present invention.

The second exemplified embodiment of an implant body for surgery of the paranasal sinuses is illustrated in FIG. 10, wherein one surface layer s consists of a highly bioactive glass ceramic and the other surface layer t of a biocompatible micaceous-cordierite-glass ceramic. Both surface layers (s and t) are interconnected to one another on their phase boundary, as already described in the first exemplified embodiment.

We claim:

1. Micaceous-cordierite-glass ceramic having a fracture toughness $K_{IC}$ of up to 2.0 MPa $m^{\frac{1}{2}}$, a hardness $HV_{0.07}$ of 300–1000, a compressive strength of up to 450 $N/mm^2$, a linear thermal expansion coefficient of $75–125 \times 10^{-7} K^{-1}$, good chemical stability and excellent machineability as well as a high resistance to abrasion, comprising a composition of said micaceous-cordierite-glass ceramic consisting essentially in weight percentages of

| | |
|---|---|
| $SiO_2$ | 43–50 |
| $Al_2O_3$ | 26–30 |
| MgO | 11–15 |
| $R_2O$ | 7–10.5 |
| $F^-$ | 3.3–4.8 |
| $Cl^-$ | 0.01–0.6 |
| CaO | 0.1–3 |
| $P_2O_5$ | 0.1–5 | wherein $R_2O$ is the sum of 3 to 5.5 wt-% $Na_2O$ and 4 to 6 wt-% $K_2O$, a first crystal phase of mica, and a second crystal phase of 5 to 30 volume-% cordierite, wherein relatively large mica crystals of 10 to 200 μm are embedded in the glass ceramic and cordierite crystals of 0.5 to 5 m are arranged in the glass ceramic.

2. Micaceous-cordierite-glass ceramic according to claim 1, further comprising relatively smaller, flat mica of 0.5 to 5 μm embedded in the glass ceramic.

3. Micaceous-cordierite-glass ceramic according to claim 1, further comprising up to 8 wt-% of a component selected from the group consisting of BaO, SrO, PbO, and mixtures thereof.

4. Micaceous-cordierlite-glass ceramic according to claim 1, further comprising up to 4 wt-% of a pigment component.

5. Micaceous-cordierite-glass ceramic according to claim 4, wherein the pigment component is selected from the group consisting of NiO, $Cr_2O_3$, $MnO_2$, FeO, $Fe_2O_3$, $TiO_2$, and mixtures thereof.

6. A stomatological composition for inlays, crowns, structures and bridges, especially of a lateral tooth area, comprising a high-strength base body; and a micaceous-cordierite-glass ceramic at least partially enclosing said high-strength base body, said micaceous-cordierite-glass ceramic having a fracture toughness $K_{IC}$ of up to 2.0 MPa $m^{178}$, a hardness $HV_{0.07}$ of 300–1000, a compressive strength of up to 450 $N/mm^2$, a linear thermal expansion coefficient of $75–125 \times 10^{-7} K^1$, good chemical stability and excellent machineability as well as high resistance to abrasion and comprising a composition of said micaceous-cordierite-glass ceramic consisting essentially in weight percentages of

| | |
|---|---|
| $SiO_2$ | 43–50 |
| $Al_2O_3$ | 26–30 |
| MgO | 11–15 |
| $R_2O$ | 7–10.5 |
| $F^-$ | 3.3–4.8 |
| $Cl^-$ | 0.01–0.6 |
| CaO | 0.01–3 |
| $P_2O_5$ | 0.1–5 | wherein $R_2O$ is the sum of 3 to 5.5 wt-% $Na_2O$ and 4 to 6 wt-% $K_2O$, a first crystal phase of mica, and a second crystal phase of 5 to 30 volume-% cordierite, wherein relatively large mica crystals of 10 to 200 μm are embedded in the glass ceramic and cordierite crystals of 0.5 to 5 um are arranged in the glass ceramic.

7. A stomatological composition according to claim 6, wherein said high-strength base body is selected from the group consisting of $Al_2O_3$ vitrified ceramic, vitrified corundum and metals.

8. A stomatological composition according to claim 6, having an external shape conforming to required anatomical characteristics.

9. A stomatological composition according to claim 6, further comprising a fracture bending strength of 200 to 400 MPa and a roughness depth of 0.15 μm.

10. A stomatological composition according to claim 6, further comprising a fixation cement for interconnecting the composition to a tooth.

11. A stomatological composition according to claim 6, further comprising a compound material for silanizing the composition for interconnection to a tooth.

12. A stomatological composition according to claim 6, wherein said micaceous-cordierite-glass ceramic further comprises relatively smaller, flat mica of 0.5 to 5 μm embedded in the glass ceramic.

13. A stomatological composition according to claim 6, wherein said micaceous-cordierite-glass ceramic further comprises up to 8 wt-% of a compound selected from the group consisting of BaO, SrO, PbO, and mixtures thereof.

14. A stomatological composition according to claim 6, wherein said micaceous-cordierite-glass ceramic further comprises up to 4 wt-% of a pigment component.

15. A stomatological composition according to claim 14, wherein said pigment component is selected from the group consisting of NiO, $Cr_2O_3$, $MnO_2$, FeO, $Fe_2O_3$, $TiO_2$, and mixtures thereof.

16. A veneer laminate for the facing of teeth made of synthetic resin, metal frames, or natural teeth, comprising
   a vestibulary layer of a micaceous-cordierite-glass ceramic,
   an oral layer of an organic synthetic material or compound material, and
   an adhesion, facilitator layer interconnecting said vestibulary and oral layers,
   wherein said micaceous-cordierite-glass cereamic has a fracture toughness $K_{IC}$ of up to 2.0 MPa m$^{\frac{1}{2}}$, a hardness $HV_{0.07}$ of 300–1000, a compressive strength of up to 450 N/mm$^2$, a linear thermal expansion coefficient of $75$–$125 \times 10^{-7}$ K$^{-1}$, good chemical stability and excellent machineability as well as a high resistance to abrasion and comprises a composition of said micaceous-cordierite-glass ceramic consisting essentially in weight percentages of

| | |
|---|---|
| SiO$_2$ | 43–50 |
| Al$_2$O$_3$ | 26–30 |
| MgO | 11–15 |
| R$_2$O | 7–10.5 |
| F$^-$ | 3.3–4.8 |
| Cl$^-$ | 0.01–0.6 |
| CaO | 0.1–3 |
| P$_2$O$_5$ | 0.1–5 | wherein R$_2$O is the sum of 3 to 5.5 wt-% Na$_2$O and 4 to 6 wt-% K$_2$O, a first crystal phase of mica, and a second crystal phase of 5 to 30 volume-% cordierite, wherein relatively large mica crystals of 10 to 200 μm are embedded in the glass ceramic and cordierite crystals of 0.5 to 5 μm are arranged in the glass ceramic.

17. A veneer laminate according to claim 16, wherein the vestibulary layer has a thickness generally equal to or less than 0.5 mm and a thickness in the area of an incisal edge greater than 0.5 mm.

18. A veneer laminate according to claim 16, further comprising at least one surface-enlarging structure on an oral side of the vestibulary layer.

19. A veneer laminate according to claim 16, wherein said micaceous-cordierite-glass ceramic further comprises relatively smaller, flat mica of 0.5 to 5 μm embedded in the glass ceramic.

20. A veneer laminate according to claim 16, wherein said micaceous-cordierite-glass ceramic further comprises up to 8 wt-% of a component selected from the group consisting of BaO, SrO, PbO, and mixtures thereof.

21. A veneer laminate according to claim 16, wherein said micaceous-cordierite-glass ceramic further comprises up to 4 wt-% of a pigment component.

22. A veneer laminate according to claim 21, wherein said pigment component is selected from the group consisting of NiO, Cr$_2$O$_3$, MnO$_2$, FeO, Fe$_2$O$_3$, TiO$_2$, and mixtures thereof.

23. Micaceous-cordierite-glass ceramic for stomatological purposes having a fracture toughness $K_{IC}$ of up to 2.0 MPa m$^{\frac{1}{2}}$, an adjustable hardness $HV_{0.07}$ of 300–800, a compressive strength of up to 450 N/mm$^2$, an adjustable linear thermal expansion coefficient of 80 to $120 \times 10^{-7}$ K$^{-1}$, good chemical stability, excellent machineability, a high resistance to abrasion, a bending fracture strength of more than 80 MPa, a hydrolytic stability of class 1 or 2, a roughness depth of 0.15 μm and X-ray opacity, comprising a compositon of said micaceous-cordierite-glass ceramic consisting essentially in weight percentages of

| | |
|---|---|
| SiO$_2$ | 43–50 |
| Al$_2$O$_3$ | 26–30 |
| MgO | 11–15 |
| R$_2$O | 7–10.5 |
| F$^-$ | 3.3–4.8 |
| Cl$^-$ | 0.01–0.6 |
| CaO | 0.1–3 |
| P$_2$O$_5$ | 0.1–5 | wherein R$_2$O is the sum of 3 to 5.5 wt-% Na$_2$O and 4 to 6 wt-% K$_2$O, a first crystal phase of mica, and a second crystal phase of 5 to 30 volume-% cordierite, wherein relatively large mica crystals of 10 to 200 μm are embedded in the glass ceramic and cordierite crystals of 0.5 to 5 μm are arranged in the glass ceramic, and wherein properties of the glass ceramic can be adjusted to the properties of natural tooth enamel, to provide a glass ceramic useful for inlays, crowns, structures and bridges, especially of a lateral tooth area.

24. A micaceous-cordierite-glass ceramic according to claim 23, having an external shape conforming to required anatomical characteristics for stomatological purposes.

25. A micaceous-cordierite-glass ceramic according to claim 23, further comprising a fixation cement for interconnecting the composition to a tooth.

26. A micaceous-cordierite-glass ceramic according to claim 23, further comprising a compound material for silanizing the composition for interconnection to a tooth.

27. Micaceous-cordierite-glass ceramic according to claim 23, further comprising relatively smaller, flat mica of 0.5 to 5 μm embedded in the glass ceramic.

28. Micaceous-cordierite-glass ceramic according to claim 23, further comprising up to 8 wt-% of a component selected from the group consisting of BaO, SrO, PbO, and mixtures thereof.

29. Micaceous-cordierlite-glass ceramic according to claim 23, further comprising up to 4 wt-% of a pigment component.

30. Micaceous-cordierite-glass ceramic according to claim 29, wherein the pigment component is selected from the group consisting of NiO, Cr$_2$O$_3$, MnO$_2$, FeO, Fe$_2$O$_3$, TiO$_2$, and mixtures thereof.

31. Micaceous-cordierite-glass ceramic having a fracture toughness $K_{IC}$ of up to 2.0 Mpa m$^{\frac{1}{2}}$, a hardness $HV_{0.07}$ of 300–1000, a compressive strength of up to 450 N/mm$^2$, a linear thermal expansion coefficient of $75$–$125 \times 10^{-7}$K$^{-1}$, good chemical stability and excellent machineability as well as a high resistance to abrasion, comprising a composition of said micaceous-cordierite-glass ceramic consisting essentially in weight percentages of

| | |
|---|---|
| SiO$_2$ | 43–50 |
| Al$_2$O$_3$ | 26–30 |
| MgO | 11–15 |
| R$_2$O | 7–10.5 |
| F$^-$ | 3.3–4.8 |
| Cl$^-$ | 0.01–0.6 |
| CaO | 0.1–3 |
| P$_2$O$_5$ | 0.1–5 | wherein R$_2$O is the sum of 3 to 5.5 wt-% Na$_2$O and 4 to 6 wt-% K$_2$O, a first crystal phase of mica, and a second crystal phase of 5 to 30 volume-% cordierite, wherein relatively large mica crystals of 10 to 200 μm are embedded in the glass ceramic and cordierite crystals of 0.5 to 5 μm are arranged in the glass ceramic, wherein said micaceous-cordierite-glass ceramic is formed in the shape of an adhesive bracket for application in dental orthopedics and orthodontics, said bracket comprising a wall thickness of at least 1 mm, a maximum height of 3 mm, a bottom portion having a length of 2.5 to 6 mm and a top wing portion, said bottom portion having a roughness of more than 5 μm, said bracket being provided with a slit having a width of 0.45 to 0.55 mm and a depth of 0.63 to 0.71 mm and extending in the direction of the length of said bottom portion, said glass ceramic adhesive bracket being machineable during clinical utilization so as to be fitted to the anatomy of a tooth.

32. A micaceous-cordierite-glass ceramic according to claim 31, wherein said bottom portion has an arched bottom surface.

33. A micaceous-cordierite-glass ceramic according to claim 31, wherein said top wing portion has bevelled edges.

34. A micaceous-cordierite-glass ceramic according to claim 31, wherein said slit is metal and traverses the top wing portion with respect to the length of the bottom portion at an angulation of up to 10° and a torque angle with respect to a plane perpendicular to the bottom portion of up to 25°.

35. Micaceous-cordierite-glass ceramic according to claim 31, further comprising relatively smaller, flat mica of 0.5 to 5 μm embedded in the glass ceramic.

36. Micaceous-cordierite-glass ceramic according to claim 31, further comprising up to 8 wt-% of a component selected from the group consisting of BaO, SrO, PbO, and mixtures thereof.

37. Micaceous-cordierite-glass ceramic according to claim 31, further comprising up to 4 wt-% of a pigment component.

38. Micaceous-cordierite-glass ceramic according to claim 37, wherein the pigment component is selected from the group consisting of NiO, $Cr_2O_3$, $MnO_2$, FeO, $Fe_2O_3$, $TiO_2$, and mixtures thereof.

39. Micaceous-cordierite-glass ceramic having a fracture toughness $K_{IC}$ of up to 2.0 MPa m$^{\frac{1}{2}}$, a hardness $HV_{0.07}$ of 300-1000, a compressive strength of up to 450 N/mm$^2$, a linear thermal expansion coefficient of $75-125\times10^{-7}$ K$^{-1}$, good chemical stability and excellent machineability as well as a high resistance to abrasion, comprising a composition of said micaceous-cordierite-glass ceramic consisting essentially in weight percentages of

| | |
|---|---|
| $SiO_2$ | 43-50 |
| $Al_2O_3$ | 26-30 |
| MgO | 11-15 |
| $R_2O$ | 7-10.5 |
| $F^-$ | 3.3-4.8 |
| $Cl^-$ | 0.01-0.6 |
| CaO | 0.1-3 |
| $P_2O_5$ | 0.1-5 | wherein $R_2O$ is the sum of 3 to 5.5 wt-% $Na_2O$ and 4 to 6 wt-% $K_2O$, a first crystal phase of mica, and a second crystal phase of 5 to 30 volume-% cordierite, wherein relatively large mica crystals of 10 to 200 μm are embedded in the glass ceramic and cordierite crystals of 0.5 to 5 μm are arranged in the glass ceramic, and wherein said micaceous-cordierite-glass ceramic is formed in the shape of an adhesive button for application in dental orthopedics and orthodontics, said button comprising a wall thickness of at least 1 mm, a maximum height of 3 mm and a base portion having base edges each measuring 2.5 to 3 mm, said base portion having a roughness of more than 5 μm, and said ceramic adhesive button being workable during clinical utilization so as to be fitted to the anatomy of a tooth.

40. A micaceous-cordierite-glass ceramic according to claim 39, wherein said adhesive button has a T-shaped configuration.

41. A micaceous-cordierite-glass ceramic according to claim 39, wherein said adhesive button has a hook configuration.

42. Micaceous-cordierite-glass ceramic according to claim 39, further comprising relatively smaller, flat mica of 0.5 to 5 μm embedded in the glass ceramic.

43. An implant material for head surgery and neck surgery, comprising a biocompatible micaceous-cordierite-glass ceramic having a fracture toughness $K_{IC}$ of up to 2.0 MPa m$^{\frac{1}{2}}$, a hardness $HV_{0.07}$ of 300-1000, a compressive strength of up to 450 N/mm$^2$, a linear thermal expansion coefficient of $75-125\times10^{-7}$ K$^{-1}$, good chemical stability and excellent machineability as well as a high resistance to abrasion comprising a composition of said micaceous-cordierite-glass ceramic consisting essentially in weight percentages of

| | |
|---|---|
| $SiO_2$ | 43-50 |
| $Al_2O_3$ | 26-30 |
| MgO | 11-15 |
| $R_2O$ | 7-10.5 |
| $F^-$ | 3.3-4.8 |
| $Cl^-$ | 0.01-0.6 |
| CaO | 0.1-3 |
| $P_2O_5$ | 0.1-5 | wherein $R_2O$ is the sum of 3 to 5.5 wt-% $Na_2O$ and 4 to 6 wt-% $K_2O$, a first crystal phase of mica, and a second crystal phase of 5 to 30 volume-% cordierite, wherein relatively large mica crystals of 10 to 200 μm are embedded in the glass ceramic and cordierite crystals of 0.5 to 5 μm are arranged in the glass ceramic.

44. An implant material according to claim 43, wherein said micaceous-cordierite-glass ceramic further comprises relatively smaller, flat mica of 0.5 to 5 μm embedded in the glass ceramic.

45. An implant material according to claim 43, wherein sasid micaceous-cordierite-glass ceramic further comprises up to 8 wt-% of a component selected from the group consisting of BaO, SrO, PbO, and mixtures thereof.

46. An implant material for head surgery and neck surgery, comprising a highly bioactive glass ceramic having machining properties, and a biocompatible micaceous-cordierite-glass ceramic having a fracture toughness $K_{IC}$ of up to 2.0 MPa m$^{\frac{1}{2}}$, a hardness $HV_{0.07}$ of 300-1000, a compressive strength of up to 450 N/mm$^2$, a linear thermal expansion coefficient of $75-125\times10^{-7}$ K$^{-1}$, good chemical stability and excellent machineability as well as a high resistance to abrasion comprising a composition of said micaceous-cordierite-glass ceramic consisting essentially in weight percentages of

| | |
|---|---|
| $SiO_2$ | 43-50 |
| $Al_2O_3$ | 26-30 |

-continued

| | |
|---|---|
| MgO | 11–15 |
| R₂O | 7–10.5 |
| F⁻ | 3.3–4.8 |
| Cl⁻ | 0.01–0.6 |
| CaO | 0.1–3 |
| P₂O₅ | 0.1–5 | wherein $R_2O$ is the sum of 3 to 5.5 wt-% $Na_2O$ and 4 to 6 wt-% $K_2O$, a first crystal phase of mica, and a second crystal phase of 5 to 30 volume-% cordierite, wherein relatively large mica crystals of 10 to 200 μm are embedded in the glass ceramic and cordierite crystals of 0.5 to 5 μm are arranged in the glass ceramic.

47. An implant material according to claim 46, wherein said bioactive glass ceramic and said biocompatible micaceous-cordierite-glass ceramic each have adjusted linear expansion coefficients whereby said implant material can be produced in a softening phase.

48. An implant material according to claim 46, further comprising at least one pigment oxide between said bioactive and said biocompatible glass ceramics for forming a visible, colored phase limit layer therebetween when said implant material is subjected to thermal treatment.

* * * * *